United States Patent [19]
Perrella et al.

[11] Patent Number: 5,888,982
[45] Date of Patent: Mar. 30, 1999

[54] REGULATION OF VASCULAR SMOOTH MUSCLE CELL HEME OXYGENASE-1

[75] Inventors: Mark A. Perrella, Brookline; Mu-En Lee, Newton, both of Mass.

[73] Assignee: President and Fellows of Harvard College, Cambridge, Mass.

[21] Appl. No.: 831,475

[22] Filed: Mar. 31, 1997

Related U.S. Application Data

[60] Provisional application No. 60/014,570 Apr. 1, 1996.
[51] Int. Cl.$^6$ .......................... A61K 39/395; A61K 48/00; C12Q 1/02; C12Q 1/68
[52] U.S. Cl. .............................................. 514/44; 424/450
[58] Field of Search ................................ 424/450; 514/44

[56] References Cited

U.S. PATENT DOCUMENTS

| 3,625,214 | 12/1971 | Higuchi . |
| 4,789,734 | 12/1988 | Pierschbacher . |
| 4,925,673 | 5/1990 | Steiner et al. . |
| 5,055,447 | 10/1991 | Palladino et al. . |

FOREIGN PATENT DOCUMENTS

| WO 89/07136 | 8/1989 | WIPO . |
| WO 95/26745 | 10/1995 | WIPO . |

OTHER PUBLICATIONS

Abraham et al., "Identification of Heme Oxygenase and Cytochrome P–450 in the Rabbit Heart", *J. Mol. Cell Cardiol.* 19:73–81 (1987).
Camhi et al., "Induction of Heme Oxygenase–1 Gene Expression by Lipopolysaccharide Is Mediated by AP–1 Activation", *Am. J. Respir. Cell Mol. Biol.*, 13:387–398 (1995).
Morrow et al., "Gene Targeting in Mammalian Cells by Homologous Recombination," *Current Opinion in Biotechnology*, 4:577–582 (1993).
Shibahara et al., "Structural Organization of the Human Heme Oxygenase Gene and the Function of its Promoter" *Eur. J. Biochem.* 179:557–563 (1989).
Vile et al., "Heme Oxygenase 1 Mediates an Adaptive Response to Oxidative Stress in Human Skin Fibroblasts", *Proc. Natl. Acad. Sci. USA*, 91:2607–2610 (1994).
Crooke, "Therapeutic Applications of Oligonucleotides", *Annu. Rev. Pharmacol. Toxicol.*, 32:329–76 (1992).
Dolnick, "Commentary: Antisense Agents in Pharmacology", *Biochem. Pharmacol.*, 40:671–75 (1990).
Glauser et al., "Septic Shock: Pathogenesis", *Lancet*, 338:732–36 (1991).
Gregoriadis, "Liposomes", *Drug Carriers in Biology and Medicine*, Ch. 14, pp. 287–341, Academic Press, (1979).
Johnson et al., "A Heme Oxygenase Product, Presumably Carbon Monoxide, Mediates a Vasodepressor Function in Rats", *Hypertension*, 25:166–169 (1995).
Kotin et al., "Site–Specific Integration by Adeno–associated Virus", *PNAS USA*, 87:2211–15 (1990).

Lavrovsky et al., "Identification of Binding Sites for Transcription Factors NF–kappa–B and AP–2 in the Promoter Region of the Human Heme Oxygenase 1 Gene", *PNAS USA*, 91(13):5987–91 (1994).
Le Doan et al., "Antisense Oligonucleotides as Potential Antiviral and Anticancer Agents", *Bull. Cancer*, 76:849–52 (1989).
Lu et al., "Gene Transfer into Hepatocytes Using a Defective Herpes Simplex Viral Vector", *Abstracts of the Meeting on Gene Therapy*, Sep. 22–26, Abstract p. 66, Cold Spring Harbor Laboratory, Cold Spring Harbor, NY, 1992.
MacMicking et al., "Altered Responses to Bacterial Infection and Endotoxic Shock in Mice Lacking Inducible Nitric Oxide Synthase", *Cell*, 81:641–50 (1995).
Marui et al., "Vascular Cell Adhesion Molecule–1 (VCAM–1) Gene Transcription and Expression Are Regulated Through an Antioxidant–sensitive Mechanism in Human Vascular Endothelial Cells", *J. Clin. Invest.*, 92:1866–74, (1993).
Melani et al., "Inhibition of Proliferation by c–myb Antisense Oligodeoxynucleotides in Colon Adenocarcinoma Cell Lines That Express c–myb1", *Cancer Res.*, 51:2897–901 (1991).
Morita et al., "Smooth Muscle Cell–derived Carbon Monoxide is a Regulator of Vascular cGMP", *PNAS USA*, 92:1475–79 (1995).
Morita et al., "Endothelial Cell Expression of Vasoconstrictors and Growth Factors is Regulated by Smooth Muscle Cell–derived Carbon Monoxide", *J. Clin. Invest.*, 96:2676–82 (1995).
Morsey et al., Efficient Adenoviral Gene Transduction in Human and Mouse Hepatocytes in Vitro and In Mouse Liver In Vivo, *J. Cell. Biochem.*, Supp. 17E, p. 226, (1993).
Otterbein et al., "Hemoglobin Provides Protection against Lethal Endotoxemia in Rats: The Role of Heme Oxygenase–1", *Am. J. Respir. Cell Mol. Biol.*, 13:595–601 (1995).
Parrillo, "Mechanisms of Disease: Pathogenetic Mechanisms of Septic Shock", *N. Eng. J. Med.*, 328:1471–77 (1993).
Perrella et al., "Arrest of Endotoxin–induced Hypotension by Transforming Growth Factor–B1", *PNAS USA*, 93:2054–59 (1996).
Rosenberg et al., "Gene Transfer into Humans—Immunotherapy of Patients with Advanced Melanoma, Using Tumor–Infiltrating Lymphocytes Modified by Retroviral Gene Transduction", *N. Eng. J. Med.*, 323(9):570–78 (1990).

(List continued on next page.)

Primary Examiner—Nathan M. Nutter
Attorney, Agent, or Firm—Fish & Richardson P.C.

[57] ABSTRACT

The invention features a method of inhibiting sepsis-associated hypotension in a mammal which includes the steps of identifying a mammal suffering from or at risk of developing sepsis and administering to the mammal a compound which inhibits expression of inducible heme oxygenase (HO-1). Also disclosed are screening assays useful for identifying a compound capable of inhibiting HO-1 expression or enzymatic activity.

2 Claims, 4 Drawing Sheets

OTHER PUBLICATIONS

Shibahara et al., "Functional Analysis of cDNAs for Two Types of Human Heme Oxygenase and Evidence for Their Separate Regulation", *J. Biochem.*, 113(2):214–18 (1993).

Trakshel et al., "Multiplicity for Heme Oxygenase Isozymes. HO–1 and HO–2 are Different Molecular Species in Rat and Rabbit", *J. Biological Chem.*, 264(2):1323–28 (1989).

Uhlman et al., "Antisense Oligonucleotides: A New Therapeutic Principle", *Chem. Rev.*, 90(4):544–84 (1990).

Tidd, "A Potential Role for Antisense Oligonucleotide Analogues in the Development of Oncogene Targeted Cancer Chemotherapy", *Anticancer Res.*, 10:1169–82 (1990).

Wei et al., "Altered Immune Responses in Mice Lacking Inducible Nitric Oxide Synthase", *Nature*, 375:408–11 (1995).

Williams et al., "Introduction of Foreign Genes into Tissues of Living Mice by DNA–coated Microprojectiles", *PNAS USA*, 88:2726–29 (1991).

Yoshida et al., "Human Heme Oxygenase cDNA and Induction of its mRNA by Hemin", *Eur. J. Biochem.*, 171:457–61 (1988).

Zakhary et al., "Heme Oxygenase 2: Endothelial and Neuronal Localization and Role in Endothelium–dependent Relaxation", *PNAS USA*, 93:795–98 (1996).

GenBank Accession No. X06985, Yoshida et al., "Human Heme Oxygenase cDNA and Induction of its mRNA by Hemin", *Eur. J. Biochem.*, 171:457–61 (1988).

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1550 base pairs
        ( B ) TYPE: nucleic acid
        ( C ) STRANDEDNESS: double
        ( D ) TOPOLOGY: linear     ( i i ) MOLECULE TYPE: cDNA     ( x i ) SEQUENCE DESCRIPTION: SEQ ID NO:1:

```
TCAACGCCTG  CCTCCCCTCG  AGCGTCCTCA  GCGCAGCCGC  CGCCCGCGGA  GCCAGCACGA      60

ACGAGCCCAG  CACCGGCCGG  ATGGAGCGTC  CGCAACCCGA  CAGCATGCCC  CAGGATTTGT     120

CAGAGGCCCT  GAAGGAGGCC  ACCAAGGAGG  TGCACACCCA  GGCAGAGAAT  GCTGAGTTCA     180

TGAGGAACTT  TCAGAAGGGC  CAGGTGACCC  GAGACGGCTT  CAAGCTGGTG  ATGGCCTCCC     240

TGTACCACAT  CTATGTGGCC  CTGGAGGAGG  AGATTGAGCG  CAACAAGGAG  AGCCCAGTCT     300

TCGCCCCTGT  CTACTTCCCA  GAAGAGCTGC  ACCGCAAGGC  TGCCCTGGAG  CAGGACCTGG     360

CCTTCTGGTA  CGGGCCCCGC  TGGCAGGAGG  TCATCCCCTA  CACACCAGCC  ATGCAGCGCT     420

ATGTGAAGCG  GCTCCACGAG  GTGGGGCGCA  CAGAGCCCGA  GCTGCTGGTG  GCCCACGCCT     480

ACACCCGCTA  CCTGGGTGAC  CTGTCTGGGG  GCCAGGTGCT  CAAAAAGATT  GCCAGAAAG     540

CCCTGGACCT  GCCCAGCTCT  GGCGAGGGCC  TGGCCTTCTT  CACCTTCCCC  AACATTGCCA     600
```

| | | | | | | |
|---|---|---|---|---|---|---|
| GTGCCACCAA | GTTCAAGCAG | CTCTACCGCT | CCCGCATGAA | CTCCCTGGAG | ATGACTCCCG | 660 |
| CAGTCAGGCA | GAGGGTGATA | GAAGAGGCCA | AGACTGCGTT | CCTGCTCAAC | ATCCAGCTCT | 720 |
| TTGAGGAGTT | GCAGGAGCTG | CTGACCCATG | ACACCAAGGA | CCAGAGCCCC | TCACGGGCAC | 780 |
| CAGGGCTTCG | CCAGCGGGCC | AGCAACAAAG | TGCAAGATTC | TGCCCCCGTG | GAGACTCCCA | 840 |
| GAGGGAAGCC | CCCACTCAAC | ACCCGCTCCC | AGGCTCCGCT | TCTCCGATGG | GTCCTTACAC | 900 |
| TCAGCTTTCT | GGTGGCGACA | GTTGCTGTAG | GGCTTTATGC | CATGTGAATG | CAGGCATGCT | 960 |
| GGCTCCCAGG | GCCATGAACT | TTGTCCGGTG | GAAGGCCTTC | TTTCTAGAGA | GGGAATTCTC | 1020 |
| TTGGCTGGCT | TCCTTACCGT | GGGCACTGAA | GGCTTTCAGG | GCCTCCAGCC | CTCTCACTGT | 1080 |
| GTCCCTCTCT | CTGGAAAGGA | GGAAGGAGCC | TATGGCATCT | TCCCCAACGA | AAAGCACATC | 1140 |
| CAGGCAATGG | CCTAAACTTC | AGAGGGGGCG | AAGGGGTCAG | CCCTGCCCTT | CAGCATCCTC | 1200 |
| AGTTCCTGCA | GCAGAGCCTG | GAAGACACCC | TAATGTGGCA | GCTGTCTCAA | ACCTCCAAAA | 1260 |
| GCCCTGAGTT | TCAAGTATCC | TTGTTGACAC | GGCCATGACC | ACTTTCCCCG | TGGGCCATGG | 1320 |
| CAATTTTTAC | ACAAACCTGA | AAAGATGTTG | TGTCTTGTGT | TTTTGTCTTA | TTTTTGTTGG | 1380 |
| AGCCACTCTG | TTCCTGGCTC | AGCCTCAAAT | GCAGTATTTT | TGTTGTGTTC | TGTTGTTTTT | 1440 |
| ATAGCAGGGT | TGGGGTGGTT | TTTGAGCCAT | GCGTGGGTGG | GGAGGGAGGT | GTTTAACGGC | 1500 |
| ACTGTGGCCT | TGGTCTAACT | TTTGTGTGAA | ATAATAAACA | ACATTGTCTG | | 1550 |

( 2 ) INFORMATION FOR SEQ ID NO:2:

( i ) SEQUENCE CHARACTERISTICS:
        ( A ) LENGTH: 7 base pairs
        ( B ) TYPE: nucleic acid
        ( C ) STRANDEDNESS: double
        ( D ) TOPOLOGY: linear     ( i i ) MOLECULE TYPE: Genomic DNA     ( x i ) SEQUENCE DESCRIPTION: SEQ ID NO:2:

TGTGTCA                                                                                                     7

( 2 ) INFORMATION FOR SEQ ID NO:3:

( i ) SEQUENCE CHARACTERISTICS:
        ( A ) LENGTH: 7 base pairs
        ( B ) TYPE: nucleic acid
        ( C ) STRANDEDNESS: double
        ( D ) TOPOLOGY: linear     ( i i ) MOLECULE TYPE: Genomic DNA     ( x i ) SEQUENCE DESCRIPTION: SEQ ID NO:3:

TGAGTCA                                                                                                     7

REGULATION OF VASCULAR SMOOTH MUSCLE CELL HEME OXYGENASE-1

This invention was made with government support under National Institutes of Health grant KO8HL03194. The U.S. government has certain rights in the invention.

This application claims priority from provisional application 60/014,570, filed on Apr. 1, 1996.

BACKGROUND OF THE INVENTION

The field of invention is treatment for hypotension.

Septic shock, the most common cause of death in intensive care units, is characterized by severe and often irreversible hypotension (Parrillo, *J. E.*, 1993, *N. Engl. J. Med.* 328:1471–1477). Sepsis leading to shock may be a detrimental consequence of a severe gram negative bacterial infection. Endotoxic shock is initiated by the release of bacterial cell wall-derived lipopolysaccharide (LPS, also known as endotoxin) and the subsequent production of cytokines and vasoactive mediators that result in vascular smooth muscle cell relaxation and hypotension (Glauser et al., 1991, Lancet 338:732–736).

SUMMARY OF THE INVENTION

It has now been discovered that inducible heme oxygenase (HO-1) transcription and enzymatic activity are markedly increased in response to LPS, suggesting that HO-1 generated carbon monoxide (CO) contributes to the reduction in vascular tone during sepsis. Inhibition of sepsis-induced hypotension can be achieved by contacting the vascular cells with a compound that inhibits HO-1 transcription and/or enzymatic activity.

The invention features a method of inhibiting sepsis-associated hypotension in a mammal, e.g., a human patient, which includes the steps of identifying a mammal at risk of developing sepsis and administering to the mammal a compound which inhibits expression of HO-1. A mammal, such as a rat, mouse, rabbit, guinea pig, hamster, cow, pig, horse, goat, sheep, dog, cat, or human, at risk of developing sepsis is one that has severe inflammation, e.g., due to infection by a bacterial, fungal, or viral pathogen. For example, hypotension associated with sepsis may be induced by a component of gram negative bacterial pathogens such as endotoxin, or by components produced by gram positive bacterial pathogens, viruses, and fungi, e.g., exotoxins which are secreted by such pathogens. Hypotension may also be induced by other inflammation-associated factors, such as cytokines, e.g., interleukin 1-β (IL1-β) or tumor necrosis factor-α (TNF-α).

Preferably, the compound selectively inhibits HO-1 expression or activity, i.e., it inhibits expression of HO-1 without significantly inhibiting expression of non-inducible heme-oxygenase (HO-2). For example, the compound may inhibit HO-1 transcription in a mammalian vascular cell such as an aortic smooth muscle cell or endothelial cell by reducing HO-1 promoter activity, e.g., by blocking the binding of trans-acting transcription factors to HO-1 promoter sequences. Alternatively, the compound may inhibit HO-1 expression by inhibiting translation of HO-1 mRNA. For example, antisense therapy may be carried out by administering a single stranded nucleic acid complementary at least a portion of HO-1 mRNA to interfere with the translation of mRNA into protein, thus reducing the amount of functional HO-1 produced by the cell.

Also within the invention is a method of inhibiting sepsis-associated hypotension in a mammal which includes the steps of identifying a mammal at risk of developing sepsis and administering to the mammal a compound which inhibits the enzymatic activity of HO-1. The enzymatic activity of HO-1 is defined as the ability to generate carbon monoxide and/or bilirubin by catabolism of heme. For example, an antibody which binds to at or near the active site of HO-1 may be administered to reduce the enzymatic activity of HO-1.

Sepsis-associated hypotension may be diagnosed in vivo by administering to a patient an HO-1 specific antibody linked to a detectable label and imaging where the label localizes in the patient. An elevated level of label in the vascular tissue of the patient compared to a normal control level indicates that the patient may be at risk of developing or is suffering from sepsis-associated hypotension.

The invention also includes screening assays to identify compounds capable of inhibiting HO-1 transcription and/or HO-1 enzymatic activity. For example, a method for determining the ability of a candidate compound to inhibit HO-1 promoter activity may include the steps of (a) providing DNA comprising a HO-1 promoter sequence linked to a reporter gene, e.g., a gene encoding a detectable marker, e.g., luciferase or alkaline phosphatase;
(b) contacting the DNA with a candidate compound; and
(c) determining the level of expression of the reporter gene.

A decrease in the level of expression in the presence of the compound, compared to the level of expression in the absence of the compound, is an indication of the ability of the candidate compound to inhibit HO-1 promoter activity. In another example, a method for determining the ability of a candidate compound to inhibit expression of HO-1 in vascular smooth muscle cells may include the steps of (a) providing a vascular smooth muscle cell; (b) contacting the cell with a candidate compound; and (c) determining the level of HO-1 expression in the cell. The method may also include the step of determining the amount of HO-2 in the vascular smooth muscle cell or a step of determining the amount of inducible nitric oxide synthase (iNOS) in the vascular smooth muscle cell. A decrease in the amount of HO-1 expression in the presence of the candidate compound compared to the amount in the absence of the candidate compound indicates that the candidate compound inhibits expression of HO-1 in vascular smooth muscle cells. A larger decrease in the amount of HO-1 expression than in HO-2 expression indicates that the candidate compound selectively inhibits HO-1 expression. A concomitant decrease in the amount of iNOS expression indicates that the candidate compound inhibits expression of both HO-1 and iNOS.

The invention also includes a transgenic non-human mammal, e.g., a rodent such as a mouse, the germ cells and somatic cells of which contain a null mutation, e.g., a deletion, in DNA encoding HO-1. By "null mutation" is meant an alteration in the nucleotide sequence that renders the gene incapable of expressing a functional protein product. The mutation could be in the HO-1 regulatory regions or in the coding sequence. It can, e.g., introduce a stop codon that results in production of a truncated, inactive gene product or it can be a deletion of all or a substantial portion of the coding sequence. For example, an exon, e.g., exon 3, of an HO-1 gene may be deleted. The invention also includes a mammalian cell line, e.g., immortalized HO-1 deficient vascular smooth muscle cells, the genomic DNA of which contains a null mutation in DNA encoding HO-1. Such cells lack the ability to synthesize enzymatically-active HO-1. The cells harboring the null mutation may be derived from a vascular smooth muscle cell obtained from a HO-1 deficient transgenic mammal.

Other features and advantages of the invention will be apparent from the following detailed description, and from the claims.

BRIEF DESCRIPTION OF THE DRAWINGS

FIG. 2 is a bar graph showing a time-course of HO-1 mRNA induction by IL-1β in RASMC. Rat aortic smooth muscle cells (RASMC) were exposed to IL-1β (10 ng/ml), and total RNA was extracted from the cells at the indicated times. RNA was also extracted from cells receiving a vehicle (control; no IL-1β) at the indicated times. Northern blot analyses were performed using 5 μg of total RNA per lane. After electrophoresis, the RNA was transferred to nitrocellulose filters which were hybridized with a $^{32}$P-labeled rat HO-1 probe. The filters were also hybridized with a $^{32}$P-labeled oligonucleotide probe complementary to 18S ribosomal RNA to assess loading differences. The signal intensity of each RNA sample hybridized to the HO-1 probe was divided by that hybridized to the 18S probe. The normalized intensities were then plotted as a percentage of vehicle.

FIG. 3 is a bar graph showing a time course of HO-2 mRNA induction by IL-1β in RASMC. Filters from the experiment shown in FIG. 2 were rehybridized with a $^{32}$P-labeled rat HO-2 probe. The signal intensity of each RNA sample hybridized to the HO-2 probe was divided by that hybridized to the 18S probe, and the normalized intensities were then plotted as a percentage of vehicle.

FIG. 4 is a bar graph showing dose-dependent HO-1 mRNA induction by IL-1β in RASMC. RASMC were treated for 8 hours with the indicated concentrations of IL-1β. Total RNA was extracted at the end of the incubation period. Northern blot analyses were performed using 5 μg of total RNA per lane. After electrophoresis, the RNA was transferred to nitrocellulose filters, which were hybridized to a $^{32}$P-labeled rat HO-1 probe. The filters were also hybridized with a $^{32}$P-labeled oligonucleotide probe complementary to 18S ribosomal RNA to assess loading differences. The signal intensity of each RNA sample hybridized to HO-1 was divided by that hybridized to the 18S probe, and the normalized intensities were then plotted as a percentage of dose 0 ng/ml.

FIG. 5 is a bar graph showing the effect of IL-1β on HO-1 mRNA transcription. Confluent RASMC were either stimulated with IL-1β or vehicle for 24 hours. Nuclei were then isolated from the RASMC, and in vitro transcription was allowed to resume in the presence of [α-$^{32}$P] UTP. Equal amounts of $^{32}$P-labeled, in vitro transcribed RNA probes from each group were hybridized to 1 μg of denatured HO-1, β-actin, and HO-2 cDNA that had been immobilized on nitrocellulose filters. The signal intensity of HO-1 was normalized by reference to the β-actin signal, and the transcriptional rate was plotted as a percentage of vehicle.

FIG. 6 is a line graph showing stability of HO-1 message, as determined by measuring mRNA levels in the presence of the transcription inhibitor actinomycin D. RASMC were stimulated with IL-1β (10 ng/ml) for 12 hours, followed by administration of actinomycin D (5 μg/ml). Total RNA was extracted from the RASMC at the indicated times after administration of actinomycin D. Northern blot analyses were performed using 5 μg of total RNA per lane. After electrophoresis, the RNA was transferred to nitrocellulose filters, which were hybridized to $^{32}$P-labeled HO-1 and 18S probes. To correct for differences in loading, the signal intensity of each RNA sample hybridized to the HO-1 probe was divided by that hybridized to the 18S probe. The normalized intensity was then plotted as a percentage of the 0-hour value against time (in log scale).

FIG. 7 is a bar graph showing the effect of cycloheximide (CHX) on HO-1 mRNA induction by IL-1β in RASMC. RASMC were exposed to no stimulus (control), IL-1β (10 ng/ml), CHX alone (10 μg/ml, CHX control), or a combination of CHX (10 μg/ml) and IL-1β (10 ng/ml). CHX was applied to the cells one-half hour before IL-1β was applied. Total RNA was extracted from the cells after 8 hours of IL-1β stimulation, and Northern blot analysis was performed using 5 μg of total RNA per lane. After electrophoresis the RNA was transferred to nitrocellulose filters, which were hybridized to $^{32}$P-labeled HO-1 and 18S probes. The signal intensity of each RNA sample hybridized to HO-1 was divided by that hybridized to the 18S probe, and the normalized intensities were then plotted as a percentage of control. The bars represent mean ± SE of three separate experiments.

DETAILED DESCRIPTION

HO generates biliverdin (which is subsequently reduced to bilirubin) and CO, a potent vasodilator that contributes to the reduction in vascular tone and hypotension associated with sepsis. HO-1 enzymatic activity was found to be upregulated within vascular tissue by a pathophysiologic process, sepsis, in vivo. LPS was found to markedly increase both HO-1 mRNA levels and HO enzymatic activity in vascular tissue in vivo, and IL-1β was found to induce HO-1 mRNA in rat aortic smooth muscle cells (RASMC) in vitro. In both large blood vessels (aorta) and small resistance vessels (arterioles), the increase in staining for HO-1 localized to vascular smooth muscle cells and endothelial cells. The induction of vascular smooth muscle cell-derived HO-1 in vitro occurred at the level of gene transcription. The antioxidants pyrrolidinedithiocarbamate (PDTC) and N-acetylcysteine (NAC) did not prevent the induction of HO-1 mRNA by IL-1β, suggesting this induction was not the result of oxidative stress.

The marked induction of HO-1 enzymatic activity within vascular tissue by LPS suggests that the CO generated by HO enzymatic activity contributes to the reduction in vascular tone during endotoxic shock. Agents which selectively inhibit HO-1 transcription and/or those which selectively inhibit HO-1 enzymatic activity, e.g., selective antagonists of HO-1, can be administered to patients to prevent and treat sepsis-associated hypotension. The role of CO in endotoxic shock was evaluated by analyzing the regulation of vascular HO-1 in vivo and investigating the mechanism of HO-1 regulation in vascular smooth muscle cells in vitro as described below.

Cell culture

RASMC were harvested from male Sprague-Dawley rats (200–250 grams) by enzymatic dissociation using standard methods. The cells were cultured in Dulbecco's modified Eagle's medium (DMEM, JRH Biosciences, Lenexa, Kans.) and supplemented with 10% fetal calf serum, penicillin (100 U/ml), streptomycin (100 μg/ml), and 25 mM Herpes (pH 7.4) (Sigma Chemical, St. Louis, Mo.). RASMC were passaged in culture every 4 to 7 days, and experiments were performed on cells which were 4 to 6 passages from primary culture. After the cells had grown to confluence, they were placed in 2% fetal calf serum 12 hours before commencement of the experiments. Salmonella typhosa LPS (Sigma Chemical) was dissolved in phosphate buffered saline and stored at −20° C. Recombinant human IL-1β (Collaborative Biomedical, Bedford, Mass.) was stored at −80° C. until use. PDTC (Sigma Chemical) was dissolved in sterile water and stored at 4° C., and NAC (L form, Chiron Therapeutics, Emeryville, Calif.) was diluted in sterile water and used immediately.

RNA blot hybridization

Total RNA was obtained from rat aortas and cultured smooth muscle cells by guanidinium isothiocyanate extraction and centrifuged through cesium chloride. The RNA was fractionated on a 1.3% formaldehyde-agarose gel and transferred to nitrocellulose filters. The filters were hybridized at 68° C. for 2 hr with $^{32}$P-labeled rat HO-1 or HO-2 probes in QuikHyb solution (Stratagene, La Jolla, Calif.). The hybridized filters were then washed in 30 mM sodium chloride, 3 mM sodium citrate, and 0.1% sodium dodecyl sulfate solution at 55° C. and autoradiographed with Kodak XAR film at −80° C. for 4 to 12 hours or stored on phosphor screens for 2 to 4 hours. To correct for differences in RNA loading, the filters were washed in a 50% formamide solution at 80° C. and rehybridized with an 18S ribosomal RNA probe. Images were displayed and radioactivity was measured on a PhosphorImager running the ImageQuant software (Molecular Dynamics, Sunnyvale, Calif.).

Induction of HO-1 mRNA by IL-1β in response to the antioxidants PDTC and NAC was measured as follows. For PDTC experiments, RASMC were exposed to no stimulus (control), IL-1β (10 ng/ml), IL-1β (10 ng/ml) plus PDTC (25 and 50 μM), or PDTC alone (25 and 50 μM). For NAC experiments, RASMC were exposed to no stimulus (control), TL-1β (10 ng/ml), IL-1β (10 ng/ml) plus NAC (5 and 25 mM), or NAC alone (5 mM). Twenty-four hours after stimulation, total RNA was extracted from the cells. Northern blot analyses were performed using 10 μg of total RNA per lane. After electrophoresis, the RNA was transferred to nitrocellulose filters, which were hybridized to $^{32}$P-labeled HO-1 and 18S probes.

Nuclear run-on analysis

RASMC were either not stimulated (vehicle) or stimulated with IL-1β (10 ng/ml) for 24 hours. The cells were subsequently lysed and nuclei were isolated as described using standard protocols. Nuclear suspension (200 μl) was incubated with 0.5 mM each of CTP, ATP, and GTP and with 125 μCi of $^{32}$P-labeled UTP (3,000 Ci/mmol) (Du Pont-New England Nuclear). The samples were extracted with phenol/chloroform, precipitated, and resuspended at equal counts/min/ml in hybridization buffer (9.7×10$^6$ cpm/ml). Denatured probes (1 μg) dot-blotted on nitrocellulose filters were hybridized at 40° C. for four days in the presence of formamide. HO-1 and HO-2 cDNA fragments were amplified from RASMC RNA by the reverse transcription polymerase chain reaction (PCR) (Morita et al., 1995, Proc. Natl. Acad. Sci. USA 92:1475–1479). HO-1 and HO-2 cDNA were used as probes to detect the presence of HO-1 and HO-2 transcripts, and β-actin cDNA was used as a control probe.

HO enzymatic activity

Aortas were harvested from rats treated with vehicle or LPS (4 mg/kg i.v.), the adventitia was stripped, and the tissue was homogenized in buffer containing 30 mM Tris, pH 7.5, 0.25M sucrose, 0.15M NaCl, and the Complete™ protease inhibitor (Boehringer Mannheim) using a Polytron™ homogenizer. The homogenate was filtered through two layers of cheesecloth, and centrifuged at 10,000× g for 15 min. The supernatant fraction was subsequently centrifuged at 100,000× g for 1 h. The microsomal pellet was resuspended in 50 mM potassium phosphate buffer (pH 7.4) containing Complete™ protease inhibitor. Heme oxygenase activity was measured by bilirubin generation using standard methods. The liver microsomal supernatant fraction from the control animal served as the source of biliverdin reductase. A reaction mixture (0.5 ml) containing 33 μM hemin, rat liver microsomal supernatant fraction (0.3 mg), NADPH generating system, and aortic microsomal protein was incubated at 37° C. for 10 min in the dark. The reaction mixture without NADPH generating system was used as a control. The reactions were stopped by placement on ice, and subsequently scanned with a spectrophotometer (Beckman, Columbia, Md.). The amount of bilirubin formed was determined as the difference in optical density units between 462nm and 530 nm (extinction coefficient, 40 nm$^{-1}$cm$^{-1}$ for bilirubin). HO enzymatic activity was expressed as nmol of bilirubin formed per mg of protein per hour. The protein concentration was determined by a dye-binding assay (Bio-Rad, Hercules, Calif.).

Immunocytochemical staining

Adult male Sprague-Dawley rats treated with LPS or vehicle were perfused with 4% paraformaldehyde. The aortas were removed, post-fixed with 4% paraformaldehyde overnight at 4° C., and then soaked in 30% sucrose for 2 days at 4° C. The specimens were cut at a thickness of 5 μm. Immunocytochemical staining of tissue sections was performed using standard methods. To reduce nonspecific binding, the sections were incubated in phosphate buffered saline containing 10% normal goat serum and 0.4% triton X-100 for 30 minutes. Rabbit polyclonal antibody against purified rat liver HO-1 (StressGen Biotechnologies, Victoria, BC, Canada) was applied for 1 hour at room temperature and then overnight at 4° C. at a dilution of 1:1000–1200. Sections were rinsed twice with high-salt phosphate buffered saline (0.5M NaCl) and once with regular phosphate buffered saline (5 minutes for each wash) and then incubated with biotinylated goat anti-rabbit IgG (Vector Labs, Burlingame, Calif.) at a dilution of 1:500 for 1 hour at room temperature. The sections were then rinsed with phosphate buffered saline and incubated with avidin-biotin complex (ABC elite kit, Vector Labs, Burlingame, Calif.) at a dilution of 1:100 for 1 hour at room temperature. After washing with PBS, the tissue sections were treated with diaminobenzidine (DAB) in phosphate buffered saline-H$_2$O$_2$ for 1–3 minutes using the peroxidase substrate kit DAB (Vector Labs, Burlingame, Calif.) and then transferred into phosphate-buffered saline solution to stop the reaction. The presence of HO-1 was indicated by the development of a brown color within the cytoplasm. Counterstaining was performed with 0.5% methyl green.

For imunocytochemical localization of HO-1 expression in vascular tissue, conscious male Sprague-Dawley rats (200–250 grams) were injected with vehicle or Salmonella typhosa LPS at a dose of 4 mg/kg i.v. The rats were killed 9 hr after vehicle or LPS administration and perfused with 4% paraformaldehyde. The aortic tissue was removed and immunocytochemical staining was performed as described above. Stained aortic tissue was viewed at ×190 magnification, and stained adventitial arterioles (vessels less than 300 μm in diameter) were viewed at ×540 magnification.

Data analysis

Comparisons between the vehicle and LPS-treated groups for HO enzymatic activity were made using unpaired t-tests (two tailed). Statistical significance was accepted for a p value <0.05.

LPS induces vascular HO-1 mRNA and enzymatic activity in vivo

Figure 1:
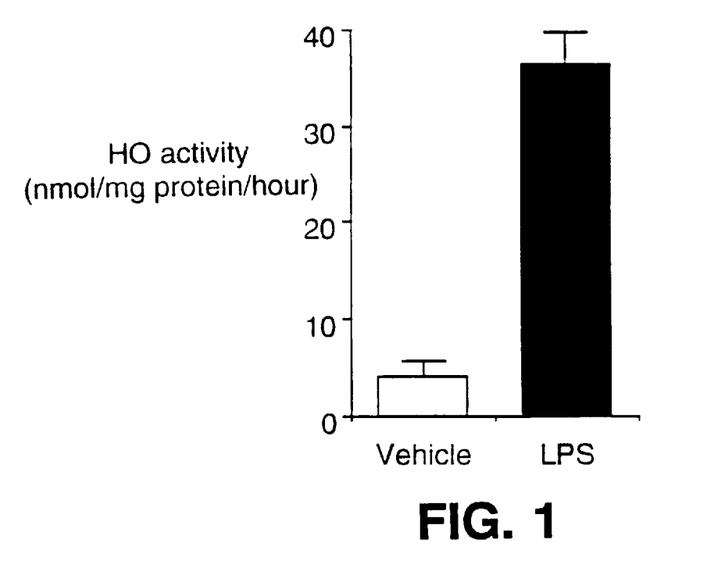
FIG. 1 is a bar graph showing induction of heme oxygenase (HO) enzymatic activity by LPS in aortic tissue in vivo. Conscious male Sprague-Dawley rats (200–250 g) were injected with *Salmonella typhosa* LPS (n=2) at a dose of 4 mg/kg intravenously (i.v.) or vehicle as a control (n=2). The rats were killed 9 hr after LPS or vehicle administration, and HO enzymatic activity was assessed in the aortic tissue. The experiment shown was performed in duplicate. HO enzymatic activity is expressed as a mean ± SD of the two experiments.

To determine if LPS regulates vascular HO-1 in an animal model of sepsis, rats were injected with vehicle or *Salmonella typhosa* LPS (4 mg/kg i.v.) as described above. HO-1 MRNA levels were found to be markedly increased in aortic tissue after 9 hours of LPS stimulation compared to the levels in tissue from rats receiving vehicle (FIG. 1). The administered dose of LPS produces hypotension in rats; the 9 hour time point at which HO-1 transcription was evaluated was chosen after performing an in vivo time course experiment. LPS was found not to induce an increase in HO-2 mRNA levels.

The following experiments were carried out to determine whether the increase in HO-1 mRNA levels corresponded to an increase in HO enzymatic activity. Rats were given vehicle or LPS (4 mg/kg i.v.), and the aortas were harvested 9 hours later (adventitia of the vessels was stripped prior to analysis). LPS promoted an 8.9-fold increase (p<0.05) in HO enzymatic activity (FIG. 1). In fact, the level of HO enzymatic activity in the aortic tissue from rats receiving LPS (36.3±2.4 nmol/mg protein/hour) was comparable to the level of HO activity in the liver of control rats (40±2.1 nmol/mg protein/hour, p=0.34). These data indicate that a significant amount of inducible HO enzymatic activity is generated in vascular tissue after LPS stimulation.

To localize the arterial cell type within the vessel responsible for the increase in HO enzymatic activity, immunocytochemical staining was performed using a rabbit anti-HO-1 antibody. Staining for HO-1 protein was increased in the smooth muscle cells of aortas from rats receiving LPS compared with rats receiving vehicle. Immunocytochemical staining demonstrated an LPS-induced increase in HO-1 expression in the smooth muscle cells of arterioles (smaller vessels that contribute to the regulation of vascular tone). Staining for HO-1 was also increased in the endothelium of aortas and arterioles after LPS stimulation.

These data indicate that HO enzymatic activity, vascular HO-1 mRNA levels, and protein levels are increased after LPS administration in vivo.

IL-1β induces HO-1, but not HO-2, mRNA in vascular smooth muscle cells in vitro

Figure 2:
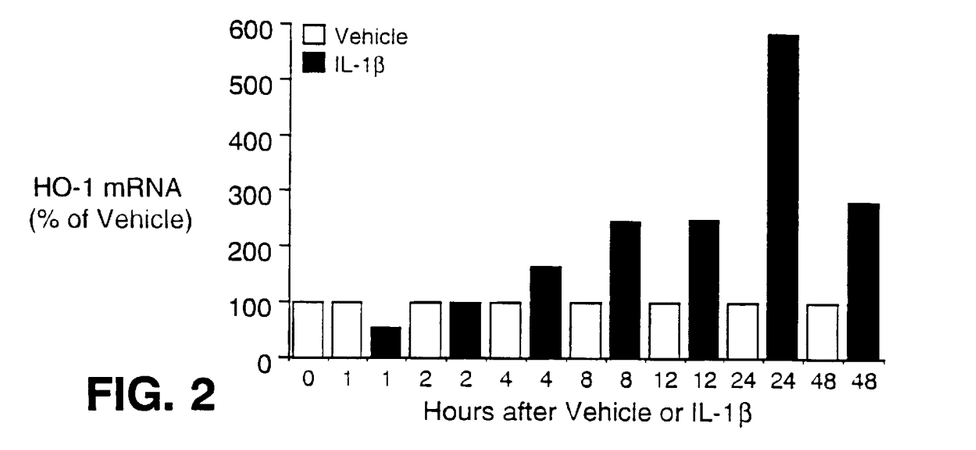
Figure 3:
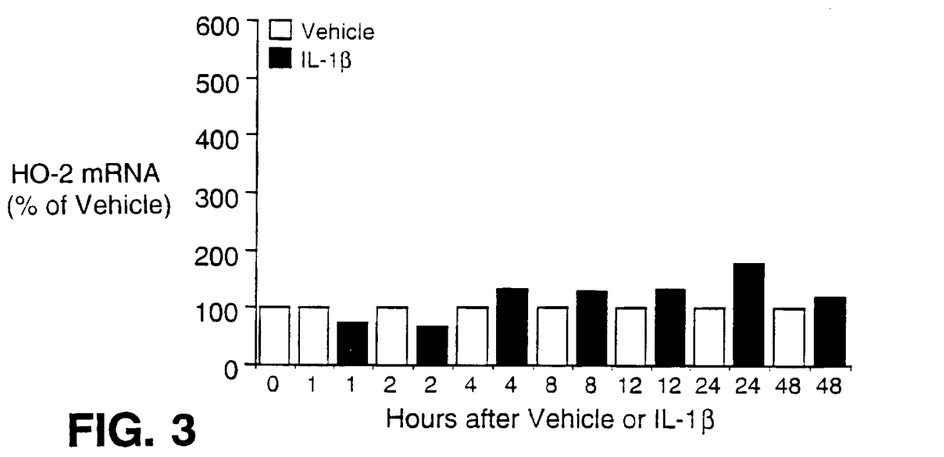

Northern blot analyses were performed with total RNA from RASMC exposed to either vehicle (control) or IL-1β. The blots were then hybridized to HO-1 and HO-2 cDNA probes. The time course (0 to 48 hours) of HO-1 mRNA stimulation by IL-1β (10 ng/ml) is shown in FIG. 2. IL-1β induced HO-1 mRNA as early as 4 hours after stimulation, and peak induction occurred after 24 hours. Twenty four hours after the administration of IL-1β, HO-1 MRNA increased by 5.8-fold compared to the control. The induction of HO-1 mRNA by IL-1β decreased to 2.8-fold after 48 hours. The message for HO-2, in contrast to HO-1, increased only minimally after treatment with IL-1β (FIG. 3).

Figure 4:
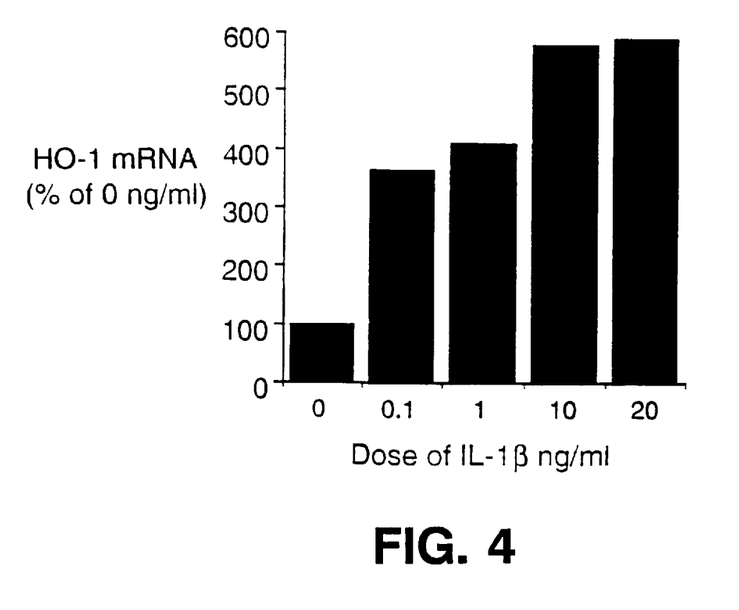
Figure 5:
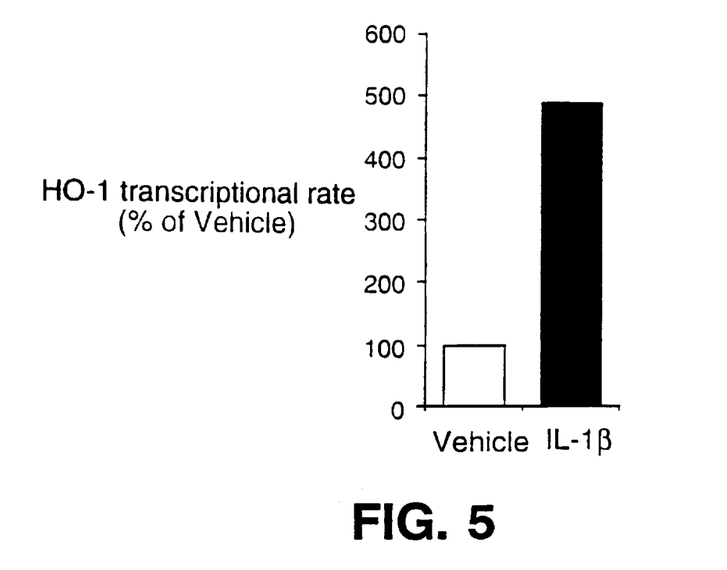

RASMC were also stimulated for 8 hours with increasing doses of IL-1β (FIG. 4). Maximal induction of HO-1 mRNA occurred at a dose of 10 ng/ml, although as little as 0.1 ng/ml promoted an increase in mRNA levels. Increasing the dose of IL-1β beyond 10 ng/ml did not further increase HO-1 MRNA levels significantly.

IL-1β increases the rate of HO-1 gene transcription

Figure 6:
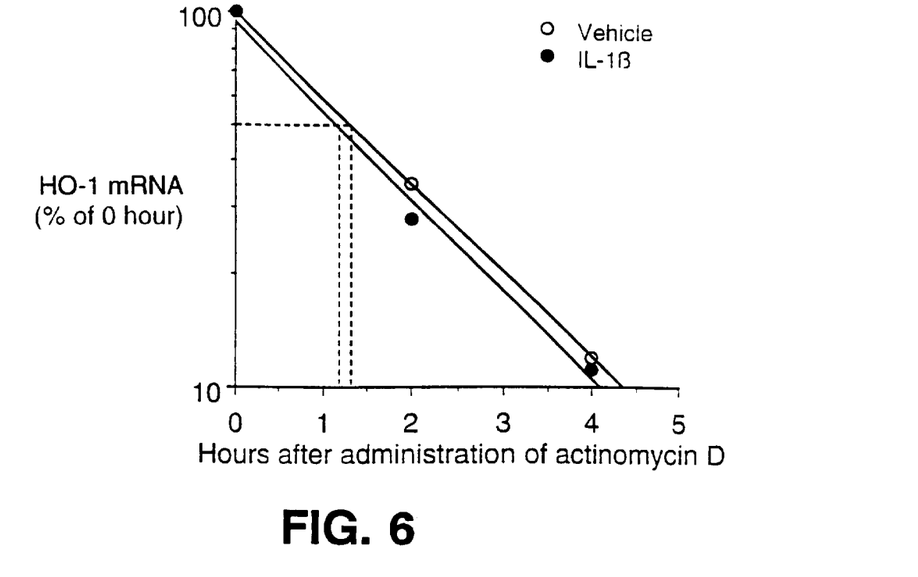

To determine the mechanism by which IL-1β increases HO-1 mRNA in vascular smooth muscle cells, experiments to assess the transcriptional rate and stability of HO-1 mRNA were performed. Nuclear run-on experiments showed a 5-fold increase in the rate of HO-1 gene transcription after 24 hours of IL-1β stimulation. Stability of HO-1 mRNA transcripts was determined by measuring mRNA levels in the presence of the transcription inhibitor actinomycin D. HO-1 mRNA was found to have a half-life of 1.3 hours after exposure to vehicle (FIG. 6). The half-life of HO-1 mRNA was not prolonged by IL-1β. These data indicate that the increase in HO-1 MRNA levels by IL-1β stimulation is the result of an increase in HO-1 gene transcription.

Induction of HO-1 mRNA by IL-1β in RASMC requires protein synthesis

Figure 7:
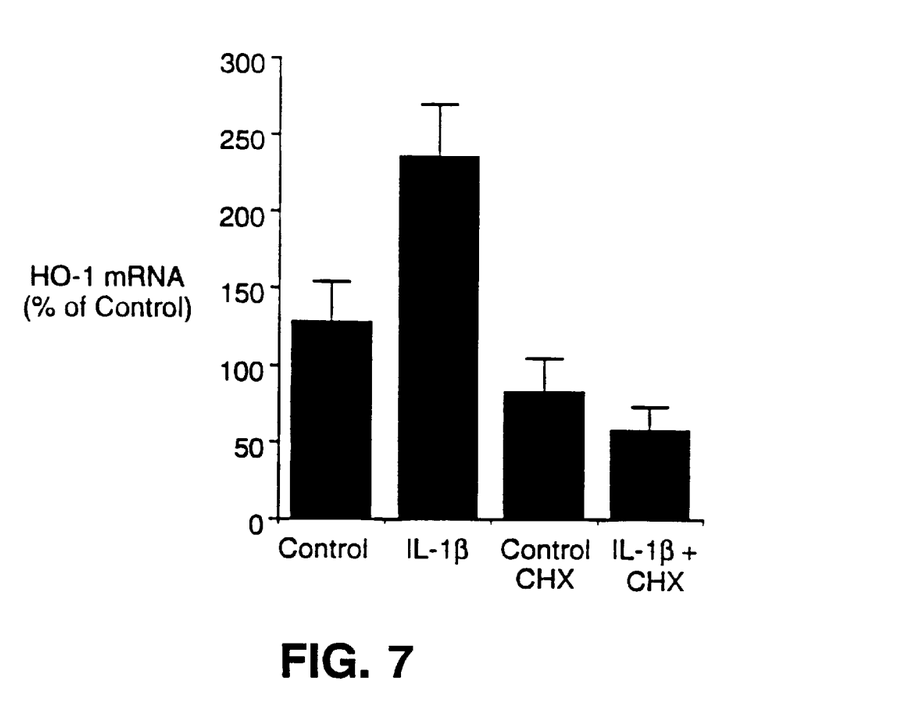

RASMC were treated with the protein synthesis inhibitor cycloheximide (10 μg/ml) for 1 hour before adding IL-1β (10 ng/ml). This dose of cycloheximide completely inhibits leucine uptake in RASMC. Cycloheximide completely inhibited the induction of HO-1 mRNA by IL-1β at 8 hours (FIG. 7). This study was also performed using another protein synthesis inhibitor, anisomycin. Anisomycin also prevented IL-1β-induced HO-1 mRNA induction. These data indicate that new protein synthesis is required for the induction of HO-1 mRNA by IL-1β in vascular smooth muscle cells.

Induction of HO-1 mRNA by IL-1β is not prevented by antioxidants

To determine if oxidative stress promotes the induction of HO-1 mRNA by IL-1β, RASMC were treated with IL-1β (10 ng/ml) for 24 hours in the presence or absence of the antioxidant PDTC (25 and 50 μM). PDTC did not inhibit IL-1β-induced HO-1 mRNA induction. This study was repeated using another antioxidant, N-acetylcysteine (NAC). NAC (5 and 25 mM) also had no effect on the induction of HO-1 mRNA by IL-1β. Previous studies have shown that comparable doses of PDTC and NAC inhibit the expression of genes upregulated by IL-1β-induced oxidative stress (Marui et al., 1993, J. Clin. Invest. 92:1866–1874). However, these data indicate that oxidative stress did not contribute to the induction of HO-1 mRNA by IL-1β in vascular smooth muscle cells.

HO-1 deficient transgenic animals

An HO-1 deficient transgenic animal, e.g., a HO-1 knockout mouse, can be produced as follows.

The murine HO-1 gene contains 5 exons and 4 introns, spanning approximately 7 kilobases (kb). The targeting construct was made by deleting the largest exon (exon 3) which contains 492 nucleotides out of the 867 nucleotides of the entire open reading frame. This deletion renders the HO-1 enzyme non-functional. A rat HO-1 cDNA was used to isolate genomic clones from a 129/SV mouse genomic library. The XhoI/BamHHI fragment of the neo cassette from pMC1neo PolyA plasmid was subcloned into pBluescript II SK (Stratagene, La Jolla, Calif.) to generate pBS-neo. To generate pBS-neo-HO-1, the 3 kb XhoI fragment of the HO-1 gene spanning from exon 1 to the end of intron 2 was subcloned into the XhoI site of pBS-neo in the same orientation as the neo cassette. The 4 kb HO-1 BamHI-EcoRI fragment containing a small portion of intron 3, exon 4, and exon 5 was subcloned into BamHI and EcoRI site of pPGK-TK to generate pPGK-TK-HO-1. The 7 kb BamHI-ClaI fragment (filled in with Klenow) from pPGK-TK-HO-1 was then subcloned into BamnI and XbaI sites (filled in with Klenow) sites of pBS-neo-HO-1 to generate the HO-1 targeting construct.

The linearized targeting construct is transfected into murine D3 embryonic stem (ES) cells, and a clone with the correct homologous recombination (yielding the appropriately disrupted HO-1 gene) injected into blastocysts and used to generate HO-1 deficient mice. HO-1 deficient mice and HO-1 deficient cell lines are useful in determining the etiology of sepsis-associated hypotension.

Therapeutic and diagnostic uses

The marked increase in HO-1 transcription and enzymatic activity suggests that HO-1-generated CO contributes to the reduction in vascular tone during endotoxic shock. Inhibition of sepsis-induced hypotension can be achieved by contacting the vascular cells with a compound that inhibits HO-1 transcription and/or enzymatic activity.

Prior to the invention, it was thought that further induction of HO-1 by hemoglobin may be of therapeutic benefit in endotoxic shock (Otterbein et al., 1995, Am. J. Respir. Cell Mol. Biol. 13:595–601) because the generation of bilirubin (which has antioxidant properties) would protect against endotoxin-induced oxidative damage in the lung. The data described herein indicates that CO production (the other product of heme metabolism), as a result of the marked induction of vascular HO-1 enzymatic activity, contributes to the decline in vascular tone during endotoxic shock and thus worsens the patient's condition.

Nucleic acids complementary to all or part of the HO-1 coding sequence (GenBank Accession No. X06985; Yoshida et al., 1988, Eur. J. Biochem. 171:457–461 (TABLE 1)) may be used in methods for antisense treatment to inhibit expression of HO-1. Antisense treatment may be carried out by administering to a mammal, such as a human, DNA containing a promoter, e.g., a vascular smooth muscle cell-specific promoter or an endothelial cell-specific promoter, operably linked to a DNA sequence (an antisense template), which is transcribed into an antisense RNA. Alternatively, as mentioned above, antisense oligonucleotides may be introduced directly into vascular smooth muscle cells. The antisense oligonucleotide may be a short nucleotide sequence (generally at least 10, preferably at least 14, more preferably at least 20 (e.g., at least 30), and up to 100 or more nucleotides) formulated to be complementary to a portion, e.g., the coding sequence, or all of HO-1 mRNA. Standard methods relating to antisense technology have been described (see, e.g., Melani et al., 1991, Cancer Res. 51:2897–2901). Following transcription of a DNA sequence into an antisense RNA, the antisense RNA binds to its target nucleic acid molecule, such as an mRNA molecule, thereby inhibiting expression of the target nucleic acid molecule. For example, an antisense sequence complementary to a portion or all of HO-1 mRNA could be used to inhibit the expression of HO-1, thereby decreasing sepsis-associated hypotension in a mammal. Oligonucleotides complementary to various sections of HO-1 mRNA can readily be tested in vitro for their ability to decrease production of HO-1, using assays similar to those described herein. Promising oligonucleotides can then be tested in vivo in rats or mice challenged with LPS.

Any vector that can transfect a vascular smooth muscle cell may be used in this method of the invention. Preferred vectors are viral vectors, including those derived from replication-defective hepatitis viruses (e.g., HBV and HCV), retroviruses (see, e.g., WO 89/07136; Rosenberg et al., 1990, N. Eng. J. Med. 323(9):570–578), adenovirus (see, e.g., Morsey et al., 1993, J. Cell. Biochem., Supp. 17E,), adeno-associated virus (Kotin et al., 1990, Proc. Natl. Acad. Sci. USA 87:2211–2215,), replication defective herpes simplex viruses (HSV; Lu et al., 1992, Abstract, page 66, Abstracts of the Meeting on Gene Therapy, Sept. 22–26, Cold Spring Harbor Laboratory, Cold Spring Harbor, N.Y.), and any modified versions of these vectors. The invention may utilize any other delivery system which accomplishes in vivo transfer of nucleic acids into eukaryotic cells. For example, the nucleic acids may be packaged into liposomes, receptor-mediated delivery systems, non-viral nucleic acid-based vectors, erythrocyte ghosts, or microspheres (e.g., microparticles; see, e.g., U.S. Pat. No. 4,789,734; U.S. Pat. No. 4,925,673; U.S. Pat. No. 3,625,214; Gregoriadis, 1979, Drug Carriers in Biology and Medicine, pp. 287–341 (Academic Press,). Alternatively, naked DNA may be administered. Delivery of nucleic acids to a specific site in the body for antisense therapy may also be accomplished using a biolistic delivery system, such as that described by Williams et al., 1991, Proc. Natl. Acad. Sci. USA 88:2726–2729.

Antisense oligonucleotides may consist of DNA, RNA, or any modifications or combinations thereof. As an example of the modifications that the oligonucleotides may contain, inter-nucleotide linkages other than phosphodiester bonds, such as phosphorothioate, methylphosphonate, methylphosphodiester, phosphorodithioate, phosphoramidate, phosphotriester, or phosphate ester linkages (Uhlman et al., 1990, Chem. Rev. 90(4):544–584; Anticancer Research, 1990, 10:1169) may be present in the oligonucleotides, resulting in their increased stability. oligonucleotide stability may also be increased by incorporating 3'-deoxythymidine or 2'-substituted nucleotides (substituted with, e.g., alkyl groups) into the oligonucleotides during synthesis, by providing the oligonucleotides as phenylisourea derivatives, or by having other molecules, such as aminoacridine or polylysine, linked to the 3' ends of the oligonucleotides (see,

TABLE 1

Human HO-1 cDNA

| 1 | tcaacgcctg | cctcccctcg | agcgtcctca | gcgcagccgc | cgcccgcgga | gccagcacga |
|---|---|---|---|---|---|---|
| 61 | acgagcccag | caccggccgg | atggagcgtc | cgcaacccga | cagcatgccc | caggatttgt |
| 121 | cagaggccct | gaaggaggcc | accaaggagg | tgcacaccca | ggcagagaat | gctgagttca |
| 181 | tgaggaactt | tcagaagggc | caggtgaccc | gagacggctt | caagctggtg | atggcctccc |
| 241 | tgtaccacat | ctatgtggcc | ctggaggagg | agattgagcg | caacaaggag | agcccagtct |
| 301 | tcgccctgt | ctacttccca | gaagagctgc | accgcaaggc | tgccctggag | caggacctgg |
| 361 | ccttctggta | cgggccccgc | tggcaggagg | tcatccccta | cacaccagcc | atgcagcgct |
| 421 | atgtgaagcg | gctccacgag | gtggggcgca | cagagcccga | gctgctggtg | gcccacgcct |
| 481 | acaccgcta | cctgggtgac | ctgtctgggg | gccaggtgct | caaaaagatt | gcccagaaag |
| 541 | ccctggacct | gcccagctct | ggcgagggcc | tggccttctt | caccttcccc | aacattgcca |
| 601 | gtgccaccaa | gttcaagcag | ctctaccgct | cccgcatgaa | ctccctggag | atgactcccg |
| 661 | cagtcaggca | gagggtgata | gaagaggcca | agactgcgtt | cctgctcaac | atccagctct |
| 721 | ttgaggagtt | gcaggagctg | ctgacccatg | acaccaagga | ccagagcccc | tcacgggcac |

TABLE 1-continued

Human HO-1 cDNA

| | | | | | |
|---|---|---|---|---|---|
| 781 | cagggcttcg | ccagcgggcc | agcaacaaag | tgcaagattc | tgcccccgtg | gagactccca |
| 841 | gagggaagcc | cccactcaac | acccgctccc | aggctccgct | tctccgatgg | gtccttacac |
| 901 | tcagctttct | ggtggcgaca | gttgctgtag | ggctttatgc | catgtgaatg | caggcatgct |
| 961 | ggctcccagg | gccatgaact | ttgtccggtg | gaaggccttc | tttctagaga | gggaattctc |
| 1021 | ttggctggct | tccttaccgt | gggcactgaa | ggctttcagg | gcctccagcc | ctctcactgt |
| 1081 | gtccctctct | ctggaaagga | ggaaggagcc | tatggcatct | tccccaacga | aaagcacatc |
| 1141 | caggcaatgg | cctaaacttc | agaggggggcg | aagggggtcag | ccctgcccctt | cagcatcctc |
| 1201 | agttcctgca | gcagagcctg | gaagacaccc | taatgtggca | gctgtctcaa | acctccaaaa |
| 1261 | gccctgagtt | tcaagtatcc | ttgttgacac | ggccatgacc | actttccccg | tgggccatgg |
| 1321 | caatttttac | acaaacctga | aaagatgttg | tgtcttgtgt | ttttgtctta | tttttgttgg |
| 1381 | agccactctg | ttcctggctc | agcctcaaat | gcagtatttt | tgttgtgttc | tgttgttttt |
| 1441 | atagcagggt | tggggtggtt | tttgagccat | gcgtgggtgg | ggagggaggt | gtttaacggc |
| 1501 | actgtggcct | tggtctaact | tttgtgtgaa | ataataaaca | acattgtctg | |

(SEQ ID NO: 1)

e.g., Anticancer Research, 1990, 10:1169–1182). Modifications of the RNA and/or DNA nucleotides may be present throughout the oligonucleotide, or in selected regions of the oligonucleotide, e.g., in the 5' and/or 3' ends. The antisense oligonucleotides may also be modified so as to increase their ability to penetrate the target tissue by, e.g., coupling the oligonucleotides to lipophilic compounds. Antisense oligonucleotides based on the HO-1 nucleotide sequence (TABLE 1) can be made by any method known in the art, including standard chemical synthesis, ligation of constituent oligonucleotides, and transcription of DNA complementary to the all or part of the HO-1 coding sequence.

HO-1 is naturally expressed and upregulated (in response to sepsis) in vascular smooth muscle cells and endothelial cells. These cells are, therefore, the preferred cellular targets for antisense therapy. Targeting of antisense oligonucleotides to vascular smooth muscle cells may be achieved, for example, by coupling the oligonucleotides to ligands of vascular smooth muscle cell receptors. Similarly, oligonucleotides may be targeted to vascular smooth muscle cells by being conjugated to monoclonal antibodies that specifically bind to vascular smooth muscle-specific cell surface proteins.

Therapeutic applications of antisense oligonucleotides in general are described, e.g., in the following review articles: Le Doan et al., Bull. Cancer 76:849–852, 1989; Dolnick, Biochem. Pharmacol. 40:671–675, 1990; Crooke, Annu. Rev. Pharmacol. Toxicol. 32, 329–376, 1992. Antisense nucleic acids may be used alone or in admixture, or in chemical combination, with one or more materials, including other antisense oligonucleotides or recombinant vectors, materials that increase the biological stability of the oligonucleotides or the recombinant vectors, or materials that increase the ability of the therapeutic compositions to penetrate vascular smooth muscle cells selectively.

Therapeutic compositions, e.g., inhibitors of HO-1 transcription or enzymatic activity, may be administered in pharmaceutically acceptable carriers (e.g., physiological saline), which are selected on the basis of the mode and route of administration and standard pharmaceutical practice. Suitable pharmaceutical carriers, as well as pharmaceutical necessities for use in pharmaceutical formulations, are described in *Remington's Pharmaceutical Sciences*, a standard reference text in this field, and in the USP/NF. The compound may be administered with intravenous fluids as well as in combination with other anti-inflammatory agents, e.g., antibiotics; glucocorticoids, such as dexamethasone (Dex). The compound may also be administered together with pressors, such as epinephrine or norepinephrine.

A therapeutically effective amount is an amount which is capable of producing a medically desirable result in a treated animal. As is well known in the medical arts, dosage for any one patient depends upon many factors, including the patient's size, body surface area, age, the particular compound to be administered, sex, time and route of administration, general health, and other drugs being administered concurrently. Dosages will vary, but a preferred dosage for intravenous administration of DNA is approximately $10^6$ to $10^{22}$ copies of the DNA molecule. The compositions of the invention may be administered locally or systemically. Administration will generally be parenterally, e.g., intravenously. As mentioned above, DNA may also be administered directly to the target site, e.g., by biolistic delivery to an internal or external target site or by catheter to a site in an artery.

Instead of inhibiting HO-1 transcription and/or translation, the enzymatic activity of HO-1 may be inhibited to treat sepsis-associated hypotension in a mammal. For example, an antibody which binds to HO-1 may be administered to reduce the enzymatic activity of HO-1. For administration to human patients, antibodies, e.g., HO-1 specific monoclonal antibodies, can be humanized by methods known in the art. Antibodies with a desired binding specificity can be commercially humanized (Scotgene, Scotland; Oxford Molecular, Palo Alto, Calif.).

Identification and use of compounds which inhibit HO-1 transcription or enzymatic activity Compounds that inhibit HO-1 transcription and/or enzymatic activity can be identified by methods ranging from rational drug design to screening of random compounds. The latter method is preferable, as simple and rapid assays for testing such compounds are available. Small organic molecules are desirable candidate compounds for this analysis, as frequently these molecules are capable of passing through the plasma membrane to inhibit HO-1 transcription within the cell.

The screening of compounds for the ability to HO-1 transcription be carried by identifying compounds that block the binding of trans-acting factors to HO-1 promoter sequences. For example, AP-1 sites in the HO-1 promoter, e.g., TGTGTCA (SEQ ID NO:2) and/or TGAGTCA (SEQ ID NO:3) which may be targets of LPS-induced trans-acting factors in vascular smooth muscle cells are linked to a functional promoter and a reporter gene, e.g., the gene encoding luciferase or alkaline phosphatase. For luciferase constructs, the cells harboring the construct are harvested after exposure to the candidate compound and luciferase activity measured; for alkaline phosphatase constructs, the culture medium of the cells is collected and the amount of alkaline phosphatase secreted by the cells into the medium is measured. Stable promoter constructs containing both SEQ ID NO:2 and SEQ ID NO:3 and constructs lacking both sequences have been made and introduced into vascular smooth muscle cells. Trans-acting factors which bind to SEQ ID NO:2 and/or SEQ ID NO:3 can be identified using these constructs.

To identify compounds capable of inhibiting HO-1 transcription, these cells containing SEQ ID NO:2 and/or SEQ ID NO:3 are contacted with candidate compounds and the ability the cells to generate the reporter protein is determined (e.g., luciferase in the cells or alkaline phosphatase in the media). A decrease in the amount of expression of the reporter protein indicates that the candidate compound inhibits HO-1 transcription.

Candidate compounds may also be screened using cell culture assays. Cells expressing HO-1, e.g., vascular smooth muscle cells, are cultured in the presence of the candidate compound. The level of expression of HO-1 in the presence and absence of the compound may be measured using known methods, e.g., PCR or Northern blot analysis to measure transcription. Western blot analysis can be used to detect the presence of the HO-1 protein.

Alternatively, bilirubin or CO production may be measured to evaluate HO-1 enzymatic activity. To identify compounds capable of inhibiting HO-1 activity, vascular smooth muscle cells, e.g., cultured cells or primary cells derived from aortic tissue, are contacted with a candidate compound. A control sample of cells is processed in parallel in the absence of a candidate compound. HO-1 enzymatic activity is measured in both samples either by measuring bilirubin as described above or CO by gas chromatography. A decrease in the amount of bilirubin or CO in the presence of the candidate compound compared to that in the absence of the candidate compound indicates that the candidate compound inhibits HO-1 enzymatic activity.

A decrease in the level of expression HO-1 indicates that the compound can inhibit sepsis-associated hypotension. Conversely, an increase in expression of HO-1 indicates that the compound can increase vascular hypotension. Such a compound can be used therapeutically to upregulate HO-1 expression, e.g., when administered locally in the lung, to treat pulmonary hypertension.

The therapeutic compounds identified using the methods of the invention may be administered to a patient by any appropriate method for the particular compound, e.g., orally, intravenously, parenterally, transdermally, transmucosally, by inhalation, or by surgery or implantation at or near the site where the effect of the compound is desired (e.g., with the compound being incorporated into a solid or semi-solid biologically compatible and resorbable matrix). Therapeutic doses are determined specifically for each compound, most being administered within the range of 0.001 to 100.0 mg/kg body weight, or within a range that is clinically determined to be appropriate by one skilled in the art.

In some cases, it may be advantageous to administer HO-1 inhibitors in combination with drugs that affect other points of a pathway leading to severe hypotension or septic shock. For example, an HO-1 inhibitor may be administered either simultaneously or sequentially with another therapeutic agent, e.g., TGFβ to inhibit iNOS or an antibiotic or anti-inflammatory drug to treat the underlying infection.

Other embodiments are within the claims.

What is claimed is:

1. A method of inhibiting sepsis-associated hypotension in a mammal, said method comprising identifying a mammal with or at risk of developing sepsis and administering to said mammal a compound which inhibits expression of inducible heme oxygenase (HO-1), wherein said compound inhibits translation of HO-1 mRNA in a vascular cell of said mammal.

2. The method of claim 1, wherein said compound consists of a single stranded nucleic acid complementary to at least a portion of said HO-1 mRNA.

* * * * *